United States Patent
Zhang et al.

(10) Patent No.: US 10,696,961 B2
(45) Date of Patent: Jun. 30, 2020

(54) MAGNETIC CELL ISOLATION TECHNIQUES

(71) Applicant: General Electric Company, Schenectady, NY (US)

(72) Inventors: Xiaohua Zhang, Schenectady, NY (US); Susumu Mine, Niskayuna, NY (US); Ye Bai, Schenectady, NY (US); Reginald Smith, Schenectady, NY (US); Minfeng Xu, Ballston Lake, NY (US); Weston Griffin, Niskayuna, NY (US); Kenneth Conway, Clifton Park, NY (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 181 days.

(21) Appl. No.: 15/829,615

(22) Filed: Dec. 1, 2017

(65) Prior Publication Data
US 2019/0169594 A1  Jun. 6, 2019

(51) Int. Cl.
*C12N 13/00* (2006.01)
*C12M 1/00* (2006.01)
(Continued)

(52) U.S. Cl.
CPC ............... *C12N 13/00* (2013.01); *B03C 1/01* (2013.01); *B03C 1/288* (2013.01); *C12M 33/00* (2013.01);
(Continued)

(58) Field of Classification Search
CPC .. C12Q 2563/143; C12N 13/00; B03C 1/288; B03C 1/01; B03C 2201/18; B03C 2201/22; B01D 21/0009; B01L 2400/043
(Continued)

(56) References Cited

U.S. PATENT DOCUMENTS

2004/0087017 A1   5/2004  Bander et al.
2006/0280727 A1  12/2006  Moore
(Continued)

FOREIGN PATENT DOCUMENTS

EP  3061529 A1  8/2016
WO  2017/035262 A1  3/2017

OTHER PUBLICATIONS

Safarikab, Ivo, et al.; "Use of Magnetic Techniques for the Isolation of Cells", Journal of Chromatography B: Biomedical Sciences, Feb. 5, 1999, pp. 33-53, vol. 722, Issue 1-2.
(Continued)

*Primary Examiner* — Claire A Norris
(74) *Attorney, Agent, or Firm* — Grogan, Tuccillo & Vanderleeden, LLP

(57) ABSTRACT

Provided are techniques that may include a disposable magnetic cell isolation holder having one or more passages that accommodate a magnetic retention material to facilitate magnetic cell isolation without adjustment of magnetic field parameters between isolation procedures using different magnetic particle sizes. When the magnetic cell isolation holder is coupled to a magnetic field generator, a first passage corresponding to a smaller particle size is positioned in a magnetic field where the magnetic field characteristics are different relative to a second passage, of a second holder or in the same holder, for use with another bead size.

20 Claims, 8 Drawing Sheets

(51) Int. Cl.
   *B03C 1/01* (2006.01)
   *B03C 1/28* (2006.01)
   *C12M 1/33* (2006.01)
   *C12M 1/26* (2006.01)

(52) U.S. Cl.
   CPC ............ *C12M 45/02* (2013.01); *C12M 47/04* (2013.01); *B03C 2201/18* (2013.01); *B03C 2201/26* (2013.01)

(58) Field of Classification Search
   USPC ................................................ 210/222, 695
   See application file for complete search history.

(56) References Cited

U.S. PATENT DOCUMENTS

| | | |
|---|---|---|
| 2010/0200405 A1 | 8/2010 | Lenz |
| 2013/0337455 A1 | 12/2013 | McNaughton et al. |
| 2014/0295426 A1 | 10/2014 | Albelda et al. |
| 2014/0302483 A1 | 10/2014 | Kauling et al. |
| 2015/0090664 A1* | 4/2015 | Nokleby .................. B01L 9/06 210/695 |
| 2015/0322424 A1 | 11/2015 | Faustman et al. |
| 2016/0187336 A1 | 6/2016 | Gue et al. |
| 2017/0037370 A1 | 2/2017 | Kaiser et al. |

OTHER PUBLICATIONS

Partington, Katherine M., et al.; "A Novel Method of Cell Separation Based on Dual Parameter Immunomagnetic well Selection", Journal of Immunological Methods, Mar. 4, 1999, pp. 195-205, vol. 223, Issue 2.

Neurauter, Axl A., et al.; "Cell Isolation and Expansion Using Dynabeads", Advances in Biochemical Engineering/Biotechnology, Aug. 7, 2007, pp. 41-73, vol. 106.

International Search Report and Written Opinion From Related International Application PCT/EP2018/083382 dated Jan. 31, 2019.

Yu Anzai et al. "Simple non-invasive cell separation method using magnetic aptamer-conjugated microbeads and nuclease digestion" The Journal of Biological Physics and Chemistry 2007 vol. 7, No. 3, pp. 83-86.

Xu Ye et al. "Aptamer-based microfluidic device for enrichment, sorting, and detection of multiple cancer cells" Analytical Chemistry, American Chemical Society, US, 2009 vol. 81, No. 17, pp. 7436-7442.

Miltenyi Biotech et al. "autoMACS Pro Separator" Sep. 1, 2017, US ISBN 978-0-7879-4736-1.

* cited by examiner

MAGNETIC CELL ISOLATION TECHNIQUES

BACKGROUND

The subject matter disclosed herein relates to the field of cell isolation and, particularly, to the field of magnetic particle-based cell selection.

Magnetic particle-based cell selection, or more simply referred to as magnetic cell isolation or magnetic cell selection, is a procedure used to isolate cells (e.g., T-cells or stem cells) from a cell mixture. In this procedure, cells in a biological sample (i.e., a cell mixture) are incubated with magnetic particles coated with antibodies or ligands designed to react with a particular surface antigen(s) of a target cell type. The antibodies or ligands recognize and bind to receptors on the surface of the target cell type, and the resulting cell suspension is passed through an external magnetic field generated by a magnetic isolation device. The target cells bound, via the antibodies or ligands, to the magnetic particles, are retained in the magnetic isolation device via magnetic force while the unlabeled cells pass through. With removal from the magnetic field, the target cells of interest can then be collected, thus isolating, or selecting out, the target cell population from the initial cell mixture.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one embodiment, a system includes a magnetic field generator configured to generate a magnetic field under magnetic field parameters, a first holder configured to be removably coupled to the magnetic field generator, and a second holder configured to be removably coupled to the magnetic field generator. The first holder has a passage configured to be positioned within the magnetic field at a first location when the first holder is coupled to the magnetic field generator. The second holder has a passage configured to be positioned within the magnetic field at a second location when the second holder is coupled to the magnetic field generator. The passage of the first holder experiences a first magnetic field strength and a first magnetic field gradient within the magnetic field generated under the magnetic field parameters at the first location. The passage of the second holder experiences a second magnetic field strength and a second magnetic field gradient within the magnetic field under the magnetic field parameters at the second location, and the second magnetic field strength is different than the first magnetic field strength, the second magnetic field gradient is different than the first magnetic field gradient, or a combination thereof.

In another embodiment, a magnetic cell isolation holder includes a body configured to be removably coupled to the magnetic field generator. The body has a first passage configured to be positioned within a magnetic field of the magnetic field generator at a first location when the holder is coupled to the magnetic field generator, and a second passage configured to be positioned within the magnetic field at a second location when the holder is coupled to the magnetic field generator. The first passage experiences a first magnetic field strength and a first magnetic field gradient within the magnetic field generated under the magnetic field parameters at the first location, and the second passage experiences a second magnetic field strength and a second magnetic field gradient within the magnetic field under the magnetic field parameters at the second location. The second magnetic field strength is different than the first magnetic field strength, the second magnetic field gradient is different than the first magnetic field gradient, or a combination thereof.

In another embodiment, a system includes a first kit having a plurality of first size beads, and a first holder having a passage configured to receive the plurality of first size beads; and a second kit having a plurality of second size beads, and a second holder having a passage configured to receive the plurality of second size beads. The passage of the first holder is positioned within the holder such that when the first holder is removably coupled to a magnetic field generator, the first holder is positioned within the magnetic field generated by the magnetic field generator at a first location. The passage of the second holder is positioned within the second holder such that when the second holder is removably coupled to the magnetic field generator, the second holder is positioned within the magnetic field generated by the magnetic field generator at a second location different than the first location. The passage of the first holder experiences a first magnetic field strength and a first magnetic field gradient within the magnetic field at the first location, and the passage of the second holder experiences a second magnetic field strength and a second magnetic field gradient within the magnetic field at the second location. The second magnetic field strength is different than the first magnetic field strength, the second magnetic field gradient is different than the first magnetic field gradient, or a combination thereof.

In another embodiment, a method for isolating target cells includes positioning a first holder having a passage within a receiving area of a frame coupled to a magnetic field generator and generating a first magnetic field in the receiving area by the magnetic field generator when the first holder is coupled to the magnetic field generator to cause the passage of the first holder to experience a first magnetic field strength, a first magnetic field gradient, or both. The method also includes positioning a second holder having a passage within the receiving area and generating a second magnetic field in the receiving area by the magnetic field generator when the second holder is coupled to the magnetic field generator to cause the passage of the second holder to experience a second magnetic field strength, a second magnetic field gradient, or both. The passage of the first holder and the passage of the second holder are positioned at different locations within the receiving area.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
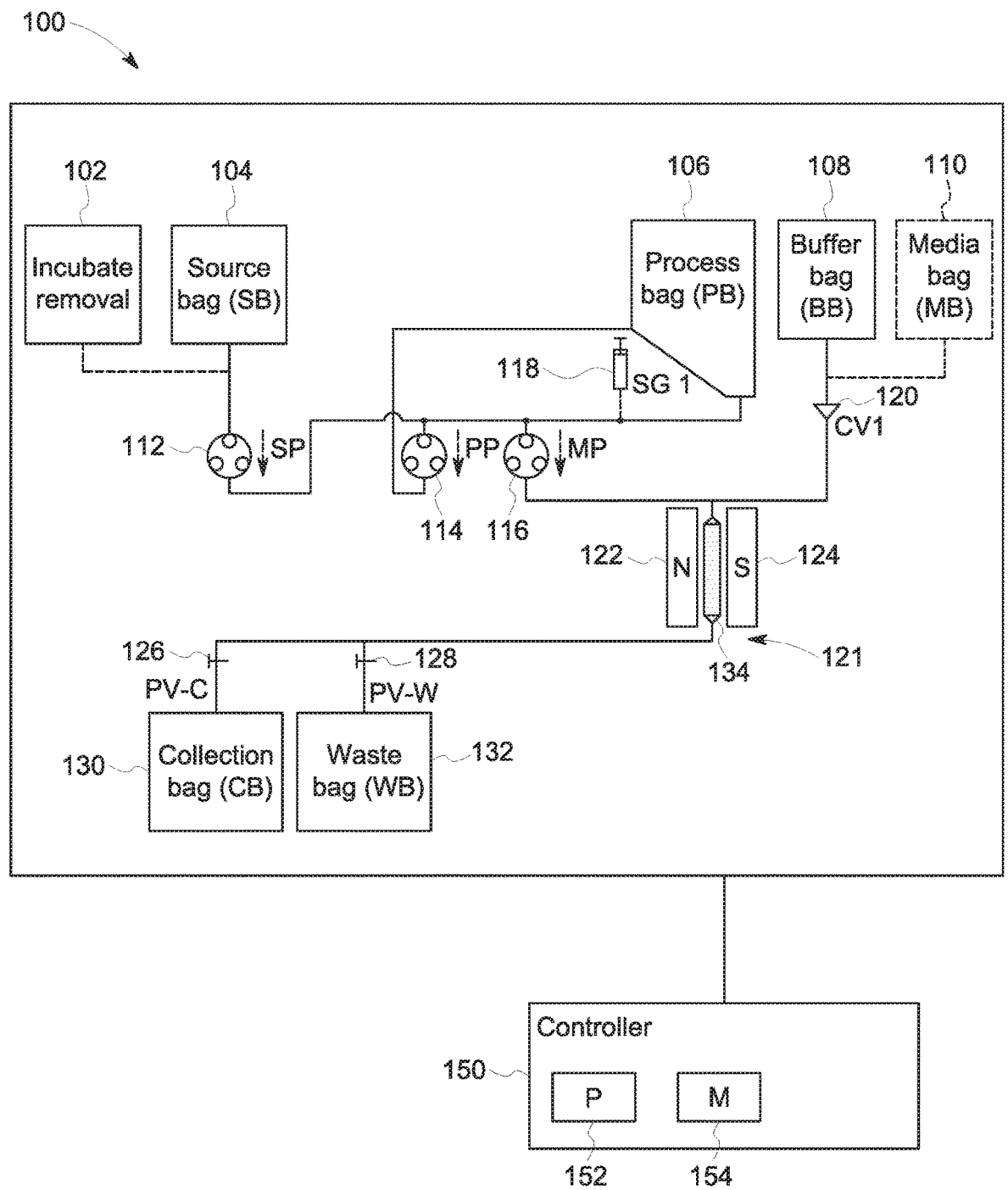
FIG. 1 is a block diagram of a magnetic particle-based cell selection system that may be used with a magnetic cell isolation holder, in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the" and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Magnetic particle-based cell selection involves isolating certain cells from a cell mixture via targeted binding of cell surface molecules to antibodies or ligands of magnetic particles (e.g., beads). Once bound, the cells coupled to the magnetic particles are able to be separated from the unbound population of cells. For example, the cell mixture including the bound and unbound cells may be passed through a separation column positioned within a magnetic field generator that captures the magnetic particles and, therefore, the associated bound cells. The unbound cells pass through the column without being captured.

Certain magnetic cell isolation techniques may incorporate nano-sized particles (e.g., beads of about 50 nm or less in diameter) while other technique may use larger particles (e.g., beads of about 2 µm or more in diameter). For example, smaller particles may be desirable because smaller particle sizes may avoid receptor activation on the target cells. Further, downstream steps may skip particle removal, because the nano-sized particles may have little effect on downstream processing or cell function. However, the smaller nano-sized magnetic particles may be separated using a magnetic cell isolation procedure that involves the use of a magnetic field gradient intensifier to amplify an applied magnetic field gradient. In contrast, larger particles have a higher magnetic moment. Thus, isolation of certain larger particles may not involve a magnetic field gradient intensifier. However, the larger particles may nonetheless be used in conjunction with additional cell-particle separation steps. Accordingly, depending on the size and/or type of magnetic particles used, the workflow, appropriate magnetic parameters, and/or the isolation device itself may vary, which adds complexity to magnetic particle-based cell isolation techniques.

In particular, because particles may vary in material and magnetic properties (including, but not limited to, size, permeability, saturation magnetization, resistivity, surface properties, and mass density), the separation conditions may also vary depending on the particle properties and may involve magnetic fields of different strengths and/or different gradients. In other words, the magnetic field parameters of a magnetic field generator may vary for magnetic cell isolation procedures using particles with differing material and magnetic properties. The present approach eliminates workflow steps of adjusting the magnetic field generator or its parameters between magnetic cell isolation procedures using particles of different sizes. In an embodiment, provided herein, a magnetic cell isolation holder is configured to be used in conjunction with a magnetic field generator such that, when used with appropriately-sized particles, the magnetic cell isolation holder positions the particles within the magnetic field at a location associated with desired magnetic field characteristics for cell separation. The magnetic field generator may apply a magnetic field using pre-set (e.g., fixed) magnetic field parameters or static magnetic field generator elements. In this manner, the operator may avoid complexities of changing the magnetic field parameters according to the selected particles. Instead, by selecting an appropriate magnetic cell isolation holder, the magnetic field experienced by the cells is appropriate for separation. Further, when using particles of different sizes and/or that involve different desired magnetic field characteristics, different magnetic cell isolation holders may be selected that position the particles at respective locations within the applied magnetic field associated with respective desired magnetic field characteristics.

For example, different magnetic cell isolation holders may be sized and shaped according to a desired positioning of cells (e.g., target cells within a cell mixture) within a magnetic field generated by a magnetic field generator. In one embodiment, each magnetic cell isolation holder includes a passageway or other cell receptacle that, when the magnetic cell isolation holder is loaded into a magnetic particle-based cell isolation system including a magnetic field generator, the cells in the magnetic field isolation holder are positioned at a location within the magnetic field with characteristics that are suitable for separation of magnetic particles of a certain type (e.g., based on particle material, shape, size, and/or size range) from the cell mixture. By selecting the magnetic cell isolation holder associated with a particular particle type, the appropriate separation may be achieved without altering settings on a magnetic isolation device or a magnetic field generator of the magnetic isolation device.

In an embodiment, an appropriate magnetic retention material, such as a separation tube or column matrix, is coupled to or positioned within a passage of a magnetic cell isolation holder and positioned at a location in the magnetic field within a magnetic field generator that corresponds to the desired magnetic field characteristics (i.e., magnetic field strength and magnetic field gradient) for the particle type used in the magnetic cell isolation procedure. The magnetic cell isolation holder and an accompanying set of particles may be provided in a kit, which may include disposable or single-use components. The kit may also include multiple sets of particles of different types and/or multiple magnetic cell isolation holders, e.g., holders optimized or designed for each set of particles.

In another embodiment, a magnetic cell isolation holder may be provided having multiple passages for use with respective different-sized particles and the user may select the appropriate passage associated with a desired particle type. For example, the magnetic cell isolation holder may have a passage (e.g., configured to accommodate a first cell separation column) at a first location for use with particles having a first diameter and a passage (e.g., configured to accommodate a second cell separation column) at a second location for use with particles having a second and larger diameter. When the magnetic cell isolation holder is inserted into the magnet cell isolation device and a magnetic field is generated, the passage at the first location may be at a position to experience a higher magnetic field strength than the passage at the second location in the magnetic cell isolation holder.

In another embodiment, a magnetic cell isolation holder may be pre-filled with the magnetic particle-cell mixture at an appropriate location associated with a desired particle type. Additionally, the magnetic cell isolation device may be part of a fluid manipulation system of a magnetic isolation system or may be functionally attached to one or more fluid manipulation systems. The magnetic cell isolation system may also include a controller configured to automatically perform the magnetic cell isolation procedure. The magnetic isolation system may be configured as a functionally-closed system.

FIG. 1 depicts a magnetic isolation system 100 that may be used in conjunction with the disclosed techniques for magnetic particle-based cell isolation system. The system 100 includes a source pump (SP) 112, a process pump (PP) 114, and a magnetic isolation pump (MP) 116. The system 100 also includes a collection pinch valve (PV-C) 126, a waste pinch valve (PV-W) 128, a particle addition syringe (SG1) 118, and a check valve (CV1) 120. In an embodiment, the check valve 120, for example, is rated at three psi cracking pressure. The system 100 may also include suitable processing and/or source vessels, e.g., sample source bag (SB) 104, process bag (PB) 106, buffer bag (BB) 108, media bag (MB) 110, collection bag (CB) 130, and waste bag (WB) 132. An incubate removal 102 may also be a bag or may be another collection vessel suitable to contain and/or dispose of the waste materials from the system 100.

The system 100 is configured to be used with a magnetic cell isolation holder 134 as provided herein. The magnetic cell isolation holder 134 may be removably coupled to (e.g., loaded into, positioned relative to) a magnetic field generator 121 (e.g., magnetic field plates 122 and 124). The system 100 may be under control of a controller 150, operating according to instructions executed by a processor 152 and stored in a memory 154. Such instructions may include the magnetic field parameters. The system 100 may include any or all the depicted components.

Figure 2:
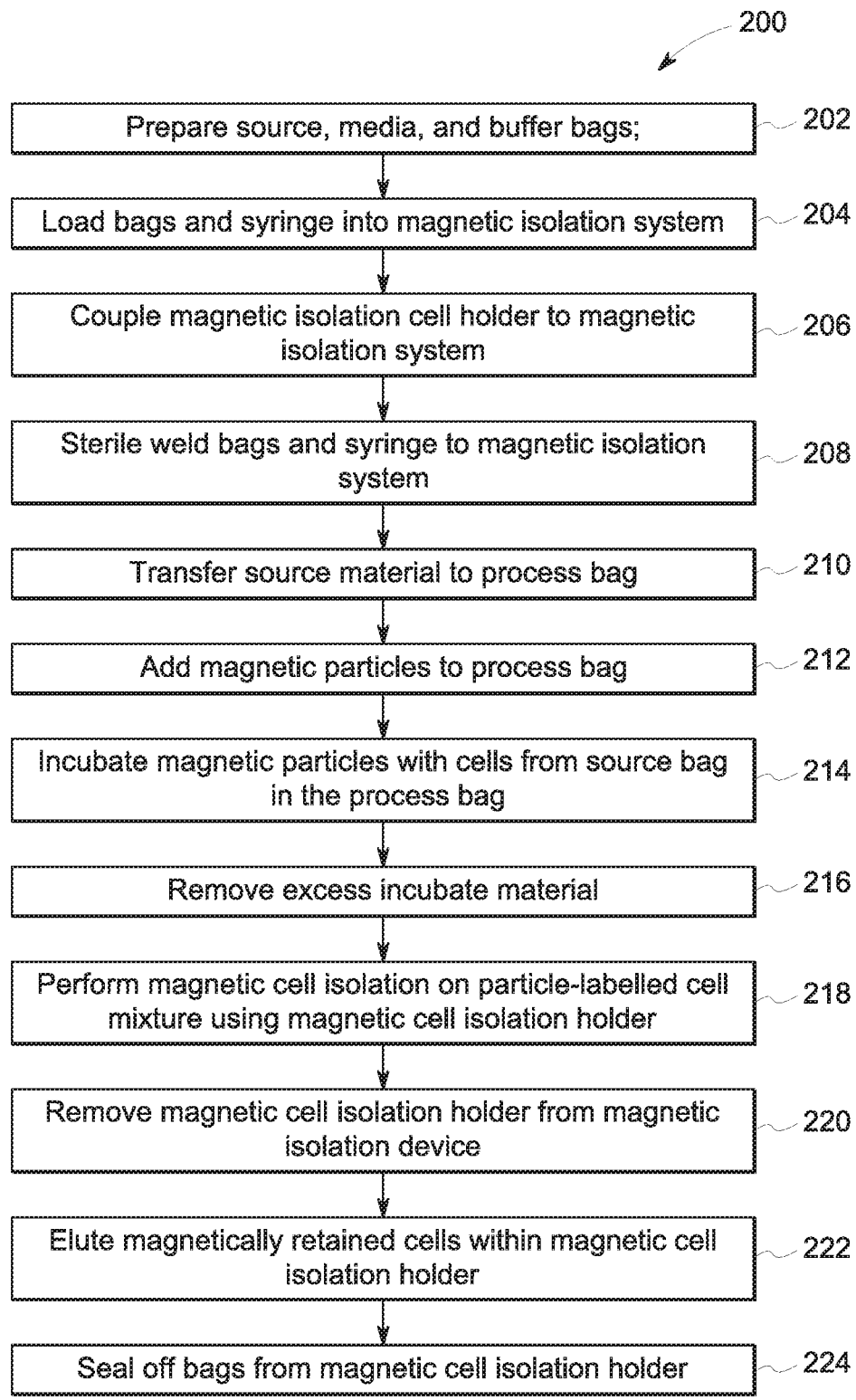
FIG. 2 is a flowchart of a method of magnetic cell isolation, in accordance with aspects of the present disclosure.

FIG. 2 depicts a flowchart for a method 200 of magnetic particle-based cell isolation that may be used with a magnetic isolation system, e.g., the system 100 of FIG. 1. It should be understood that the depicted method 200 is by way of example and that the techniques disclosed herein may be used in conjunction with other magnetic particle-based cell isolation workflows. In step 202, the source bag 104, the media bag 110, buffer bag 108, and particle addition syringe 118 are prepared for use with the magnetic isolation system. In step 204, source bag 104, media bag 110, buffer bag 108, and particle addition syringe 118 are loaded into the magnetic isolation system. Source bag 104 is fluidically coupled to source pump 112. Media bag 110 and buffer bag 108 are fluidically coupled to check valve 120. Particle addition syringe 118 is fluidically coupled to process bag 106. In step 206, a magnetic cell isolation holder 134 is coupled to (e.g., positioned adjacent to, inserted into, loaded into) the magnetic field generator 121 (e.g., magnetic field plates 122 and 124) of the magnetic isolation system 100. In step 208, the bags 104, 110, 108 and the syringe 118 are sterile welded to the magnetic isolation device. In step 210, source material, such as a cell mixture, from source bag 104 is transferred to process bag 106 via source pump 112.

In step 212, the magnetic particles (e.g., beads) within particle addition syringe 118 are added to the process bag 106. In step 214, the magnetic particles are incubated with the cell mixture in the process bag 106. The incubate material (e.g., cell mixture and particles) may be circulated in and out of the process bag 106 via process pump 114 in order to facilitate sufficient binding between the target cells and magnetic particles. In step 216, the source bag 104 is decoupled from the source pump 112 and incubate removal 102 is fluidically coupled to the source pump 112. Excess incubate material is then removed from process bag 106 via source pump 112 and deposited in incubate removal 102. In step 218, magnetic cell isolation is performed on the particle-labelled cell mixture. The magnetic cell isolation holder 134 is coupled to the magnetic field generator 121 which then generates a magnetic field under predetermined magnetic field parameters. The particle-labelled cell mixture from the process bag 106 flows through the magnetic cell isolation holder 134 via magnetic isolation pump 116. In one embodiment, the magnetic cell isolation holder 134 accommodates a magnetic retention element or material, such as a separation column, matrix, or tube. The particle-labelled cells are then magnetically retained in the tube or column matrix of the magnetic cell isolation holder 134 and any non-retained material flows through the magnetic cell isolation holder 134 to waste bag 132. In an optional step, buffer or media may rinse the process bag, and the magnetic cell isolation procedure may be repeated. In step 220, the magnetic cell isolation holder 134 is removed from the magnetic isolation device. In step 222, the retained cells are then eluted by flushing the magnetic cell isolation holder 134 with a fluid with a high flow rate, such that the viscous force of the fluid overcomes any remnant magnetic force on the retained magnetic particles. The fluid and the particle-labelled cells are then collected in collection bag 130. In step 224, the bags (e.g., collection bag 130, waste bag 132, buffer bag 108, and media bag 110) are sealed and the magnetic cell isolation holder 134 may, in one embodiment, then be disposed of.

Figure 3A:
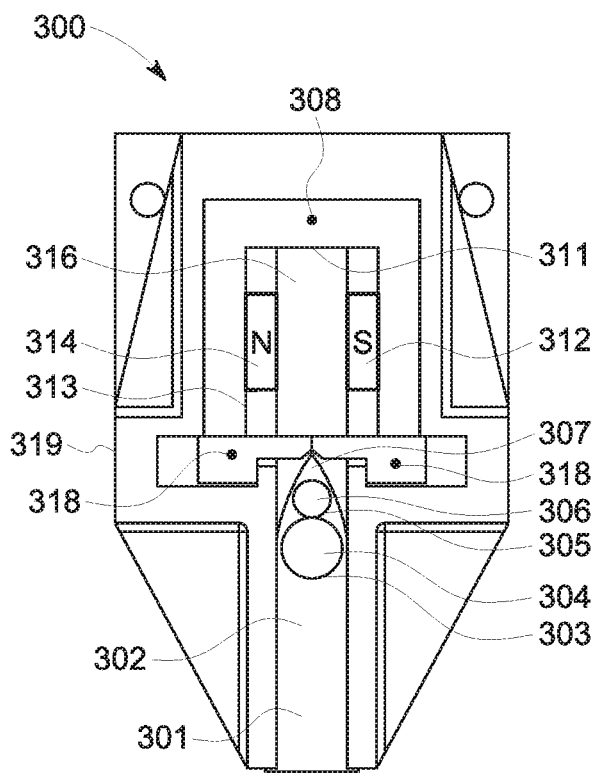
FIG. 3A illustrates a top view of an embodiment of the magnetic cell isolation holder in an unloaded configuration with respect to the magnetic field generator, in accordance with aspects of the present disclosure.
Figure 3B:
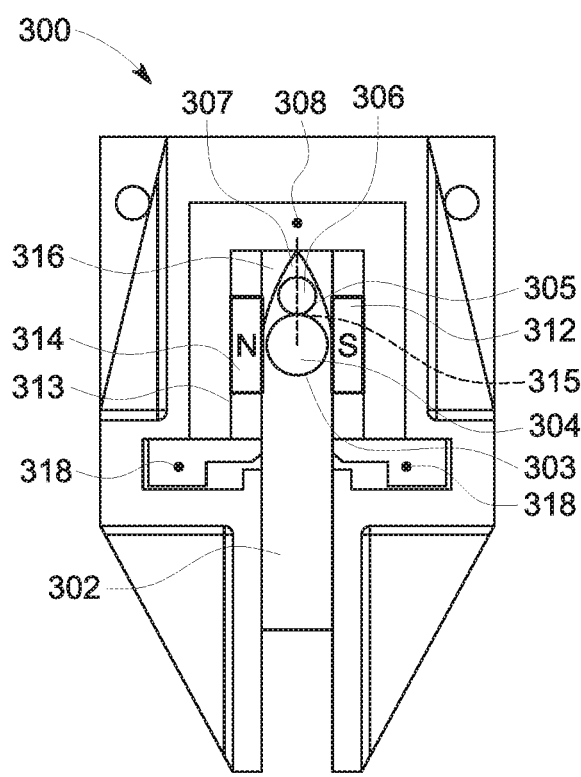
FIG. 3B illustrates a top view of an embodiment of the magnetic cell isolation holder in a loaded configuration with respect to the magnetic field generator, in accordance with aspects of the present disclosure.

FIGS. 3A and 3B illustrate top views of different configurations of a magnetic cell isolation holder 302 (e.g., magnetic cell isolation holder 134 of FIG. 1) positioned within a magnetic isolation device 300 in FIG. 3A and FIG. 3B. FIG. 3A depicts the magnetic cell isolation holder 302 in an unloaded configuration in the magnetic cell isolation device 300. The magnetic cell isolation holder 302 may include a body 301, which may be formed from any suitable nonmagnetic material configured to accommodate the cell isolation and be coupled to the magnetic isolation device 300. The magnetic cell isolation holder 302 may include one or more passages formed within or through the body 301 and through which a cell mixture may flow. While FIG. 3A shows two separate passages 303 and 305, it should be understood that the magnetic cell isolation holder 302 may include only one passage, two or more passages, etc. Turning to the passage 303, the passage 303 may be configured to accommodate a magnetic retention material 304 configured to, under the magnetic field, retain cells bound to magnetic particles and permit unbound cells to pass through. Similarly, the passage 305 may also accommodate a magnetic retention material 306. The magnetic retention material 304, 306 may be the same or different. Further, the passages 303, 305 may be differently sized and positioned relative to an end surface 307 of the body 301. For example, a distance 315 between the end surface 307 and a center point of the passage 303 may be different than a distance between other passages of the body 301 relative to the end surface 307. In this manner, a passage may experience a magnetic field that is correlated to its position within the body 301.

The end surface 307 may be configured to abut a stopping portion or surface 311 of a frame 319. The frame 319 may be configured to conduct magnetic flux. While the body 301 is shown as terminating a point at the end surface 307, it should be understood that other configurations are contemplated. FIG. 3B shows a loaded configuration in which the magnetic cell isolation holder 302 is positioned within a receiving area 316 of a magnetic field generator 313. The loading may include advancing the end surface 307 towards the stopping surface 311 until the end surface 307 abuts the stopping surface. In the loaded configuration, a portion of the body 301 may nonetheless remain outside of the receiving area 316. Accordingly, in one embodiment, the one or more passages of the body 301 may be positioned to be within the receiving area 316 when loaded.

The magnetic isolation device 300 may also include doors or other features configured to reduce leakage of the magnetic field outside of the receiving area 316. The steel backing 308 and doors 318 of the frame 319 of the magnetic isolation device 300 are made of soft magnetic material (e.g., 1018 steel). They are magnetized in the presence of a magnetic field, and demagnetized when the magnetic field is removed. When the magnetic cell isolation holder 302 is not inserted into the receiving area 316 of the magnetic field generator 313, the doors 318 of the magnetic field generator 313 close the gap with the help of a compressed spring attached to either door, thus enclosing the magnetic flux within the steel backing 308 and doors 318. This prevents the leaking of magnetic flux to the passages 303, 305 when demagnetization is desired for certain processes, such as elution.

FIG. 3B depicts the magnetic cell isolation holder 302 in a loaded configuration in the magnetic isolation device 300. When the magnetic cell isolation holder 302 is fully inserted in the receiving area 316 of the magnetic field generator 313, the position of the passages 303, 305 are defined by the geometry of the magnetic cell isolation holder 302 and the magnetic isolation device 300. A portion of the backing 308 (e.g., the stopping surface 311) of the magnetic isolation device 300 may abut a portion of the magnetic cell isolation holder 302 when the magnetic cell isolation holder 302 is fully inserted into the magnetic field generator 313. Additionally, although the magnetic cell isolation holder 302 has a tapered shape in FIGS. 3A and 3B, any suitable shape of the magnetic cell isolation holder 302 may be used.

The doors 318 of magnetic field generator 313 open to allow the insertion of the magnetic cell isolation holder 302 between the magnetic field plates 312, 314 of the magnetic field generator 313. For example, the position of passage 303 within the magnetic field generator 313 may cover the location in the magnetic field with the highest magnetic field strength (i.e., 0.5 T). In another example, the position of passage 305 within the magnetic field generator 313 may cover the location in the magnetic field with the highest magnetic field gradient (i.e., 50 T/m), while meeting the magnetic field strength requirement (i.e., 0.15 T) of the magnetic particles.

To elute the retained particles (e.g., particles or particle-bounded cells) from the magnetic retention material (e.g., magnetic retention material 304, 306), the external magnetic field may be removed by retracting the isolation holder 302 to the disengagement position (i.e., unloaded configuration of FIG. 3A). The doors close to ensure that no magnetic flux leaks out to affect the passages 303, 305 when no external magnetic field is required near the passages 303, 305. Then, a fluid with a high flow rate flows through the passages 303, 305, which generates large viscous force on the retained particles. When the viscous force is greater than the retaining force (i.e., the magnetic force due to the remnant magnetic field), the particles are washed off from the magnetic retention material of the passages 303, 305 and collected. However, in other embodiments, the applied magnetic field may be terminated under control of the controller 150.

As discussed, the magnetic cell isolation holder 302 may have one or more passages, with each passage corresponding to the type and/or the size of particles used in the magnetic cell isolation procedure. For example, the magnetic cell isolation holder 302 may have three passages: a tube for particles with a 4.5 µm diameter, a tube for particles with a 3 µm diameter, and a tube for particles with a 2 µm diameter. The passages in each magnetic cell isolation holder 302 may also be different sizes or be the same size.

Figure 4A:
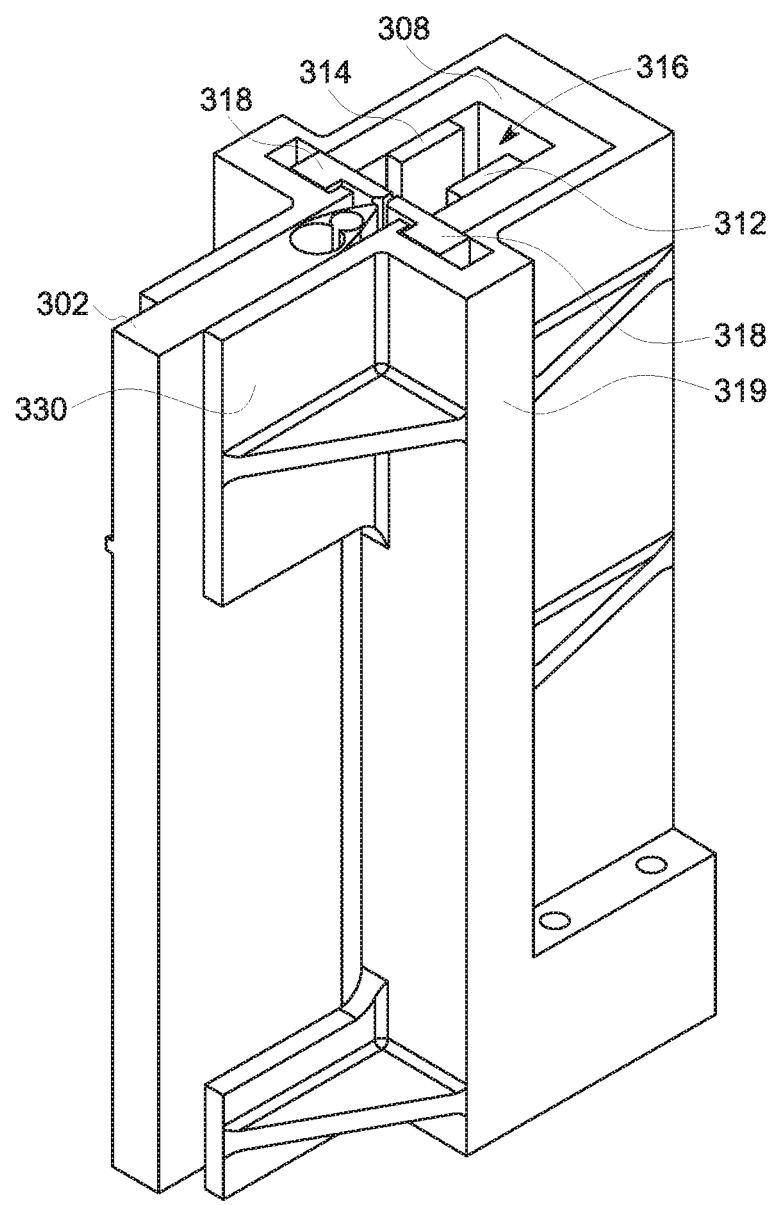
FIG. 4A illustrates a perspective view of an embodiment of the magnetic cell isolation holder in an unloaded configuration with respect to the magnetic field generator, in accordance with aspects of the present disclosure.
Figure 4B:
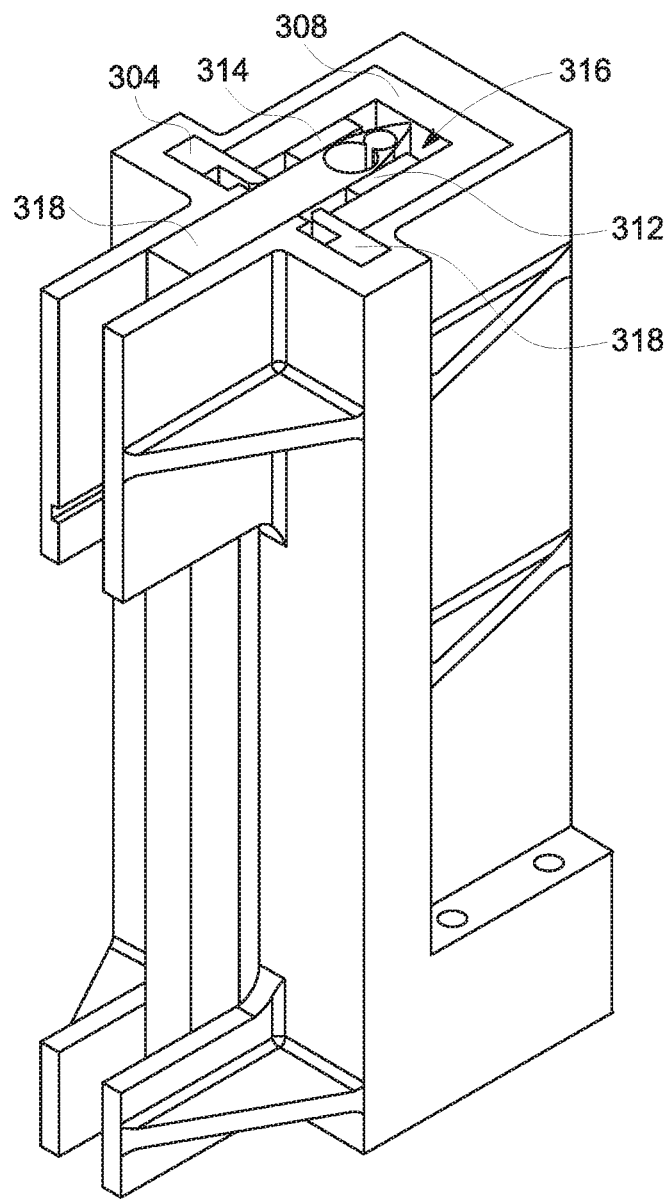
FIG. 4B illustrates a perspective view of an embodiment of the magnetic cell isolation holder in a loaded configuration with respect to the magnetic field generator in a loaded configuration, in accordance with aspects of the present disclosure.

FIGS. 4A and 4B illustrate isometric views of different configurations of the magnetic cell isolation holder and the magnetic isolation device of FIGS. 3A and 3B. FIG. 4A shows the position of the magnetic cell isolation holder 302 before engagement of the magnetic cell isolation holder 302 in the magnetic isolation device 300 for magnetic isolation. FIG. 4B shows the position of the magnetic cell isolation holder 302 after engagement of the magnetic cell isolation holder 302 in the magnetic field generator 313 for magnetic isolation. The frame 319 may include opposing guide plates 330 spaced apart from one another at a distance to permit passage of the magnetic cell isolation holder 302 therebetween and to facilitate proper positioning within the receiving area 316.

While certain disclosed techniques relate to positioning the magnetic cell isolation holder as disclosed within a fixed-position magnetic field generator, it should be understood that other implementation may be contemplated. For example, the magnetic field generator may move relative to a magnetic isolation holder loaded into a fixed-position frame.

Figure 5:
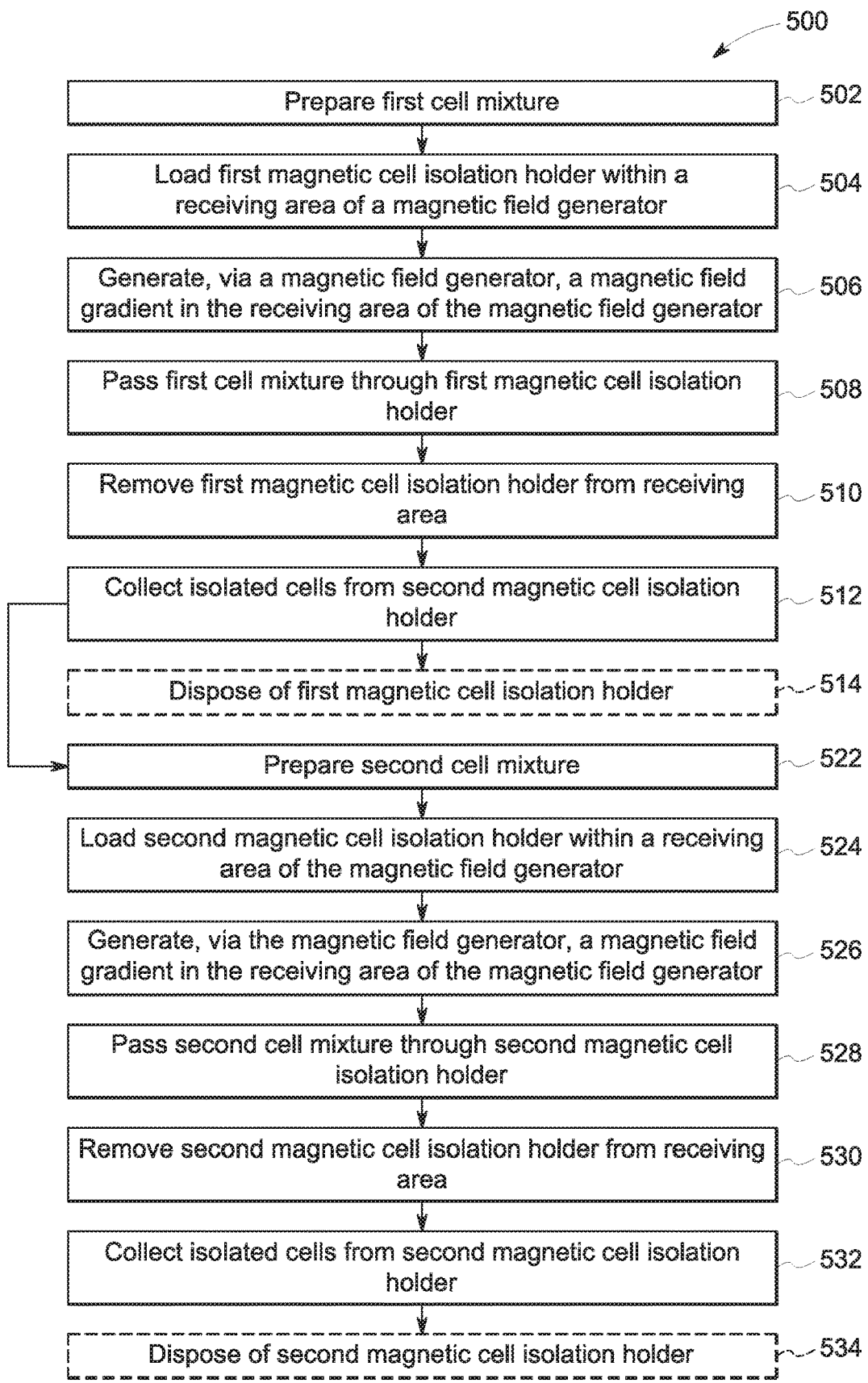
FIG. 5 is a flowchart of a method of magnetic cell isolation using different magnetic cell isolation holders, in accordance with aspects of the present disclosure.

FIG. 5 depicts a flowchart for a method 500 of magnetic cell isolation that may be used with a magnetic isolation device. In step 502, a first cell mixture is prepared by incubating the cell mixture with a set of magnetic particles having the desired characteristics (e.g., size, type, ligand, etc.). After a sufficient period of time has passed to ensure that the target cells have been labelled with the magnetic particles, the excess incubate mixture is removed. In another embodiment, part of the incubated mixture may be removed and evaluated for quality control purposes, i.e., the excess incubate mixture may be evaluated to assess binding characteristics. In step 504, a first magnetic cell isolation holder 302 may be coupled within the receiving area 316 of a magnetic field generator 313. In step 506, the magnetic field generator 313 generates a magnetic field in the receiving area 316 of the magnetic field generator 313. In step 508, the first cell mixture flows through a passage (e.g., one or more of passages 303 or 305) in the first magnetic cell isolation holder 302. The magnetic particle-labelled cells in the cell mixture are retained in the passage by a magnetic retention material (e.g., one or more of magnetic retention materials 304 or 306) of the first magnetic cell isolation holder 302 while the rest of the cell mixture material flows through the passage of the first magnetic cell isolation holder 302. In step 510, the generation of the magnetic field is stopped by removing the first magnetic cell isolation holder 302 from the receiving area 316 of the magnetic field generator 313 (or by terminating application of the magnetic field), which results in the demagnetization of the magnetic cell isolation holder 302. In step 512, the retained or isolated cells and particles from the first magnetic cell isolation holder 302 are collected by eluting the magnetically retained particles or cells in the passage of the magnetic cell isolation holder 302 with a fluid having a high flow rate or another suitable method. In step 514, optionally, the magnetic cell isolation holder 302 may be disposed of Steps 522 to 534 mirror steps 502 to 514 but may instead pass cells labelled with a set of different-sized particles in a second cell mixture through a passage in a second (i.e., different) magnetic cell isolation holder 302 or in a different passage of the first magnetic cell isolation holder 302. Although steps 522 to 534 illustrate a method using two different magnetic cell isolation holders, it should be recognized that the two magnetic cell isolation holders may instead be the same magnetic cell isolation holder having a different passage for each cell mixture. Additionally, the second cell mixture may be the resulting cell mixture that passes through the first magnetic cell isolation holder 302 from step 508 without the retained particle-labelled cells.

Magnetic selection of the target cells may be either positive or negative selection. Positive selection uses magnetic particles to label the target cells and the target cells are collected as the labelled fraction. Negative selection or depletion uses magnetic particles to label the unwanted cells and the target cells are collected as the unlabeled fraction.

Figure 6:
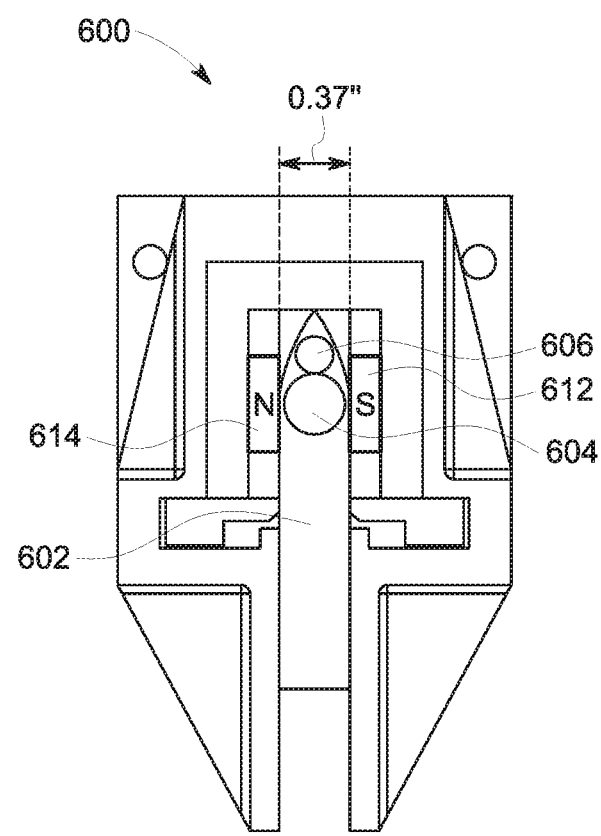
FIG. 6 illustrates a top view of an embodiment of the magnetic cell isolation holder and the magnetic field generator in a loaded configuration, in accordance with aspects of the present disclosure.

FIG. 6 illustrates a top view of the locations of the magnetic cell isolation holder 602 relative to the permanent magnets 612, 614 of the magnetic field generator 600. In one embodiment, the distance between the permanent magnets 612, 614 is 0.37 inches. However, other distances between the permanent magnets may be used depending on the configuration of the isolation device. In the depicted embodiment, the magnetic retention material may be a column matrix 604 for use with, for example, Miltenyi microbead-labelled cells, and the magnetic retention material 606 may be a tube for use with, for example, Dynabead-labelled cells. For any individual magnetic cell isolation procedure, either a column matrix or a tube may be used.

Figure 7:
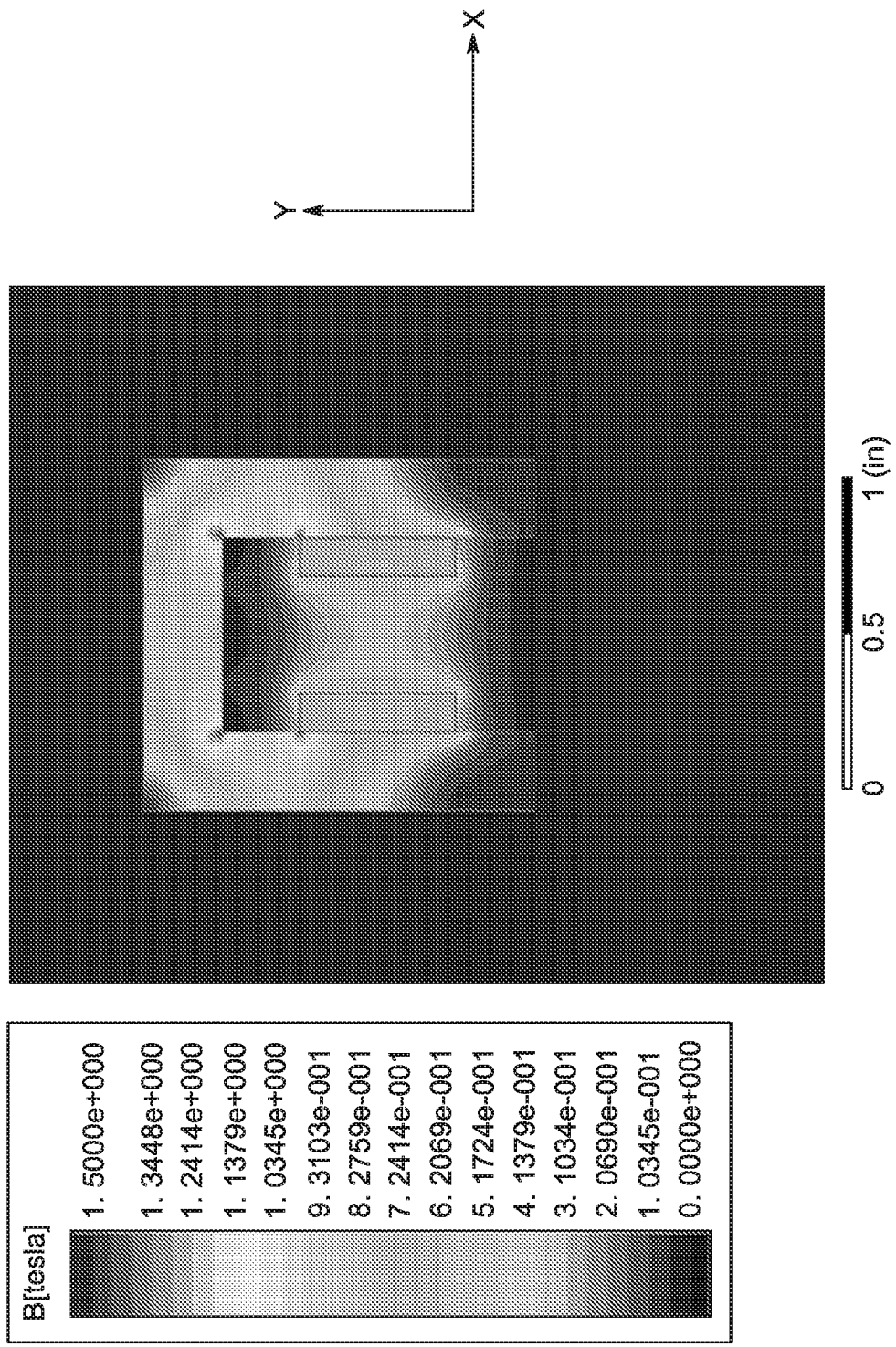
FIG. 7 is a magnetic field distribution of a magnetic field generator, in accordance with aspects of the present disclosure.

FIG. 7 depicts the magnetic field distribution with the permanent magnets and backing steel of the magnetic field generator showing different magnetic field characteristics of the magnetic field at different locations. As disclosed, the magnetic field parameters for separation are different for different-sized particles (e.g., beads). A larger particle has a higher magnetic momentum, and thus requires a lower magnetic field gradient to generate an equal amount of force, when compared with a smaller particle with a lower magnetic momentum. The magnetic force can be expressed as: $F_{mag}=M\cdot\nabla B$, where M is the magnetic momentum, and $\nabla B$ is the magnetic field gradient. To ensure the highest magnetic momentum, the magnetic material must be saturated with external field strength (i.e., 0.15 T for Dynabeads as discussed herein). When the magnetic force is greater than the viscous force in the flow field, the magnetic particles will move in the direction of the magnetic force until they reach the wall of the tube or the spheres of the column matrix.

In certain embodiments, the disclosed techniques may be used to isolate cells for chimeric antigen receptor cell therapy (or CAR-T). CAR-T involves isolating certain types of white blood cells from peripheral blood mononuclear cells (PBMCs), i.e., T-cells. The target cells (T-cells) are modified with receptors that enable them to recognize the cancer and attack it. Further, the disclosed techniques may be used in conjunction with any suitable types of particles, such as, by way of example, Miltenyi nano-sized microbeads (50 nm in diameter) and Dynabeads (4.5 μm in diameter). Miltenyi's microbeads are nano-sized, superparamagnetic beads, which require a magnetizable column matrix to retain them from a flow field. The magnetizable column matrix is constructed with soft magnetic material spheres (e.g., 0.4 mm diameter stainless steel 400 series balls). The stainless steel 400 series balls are rust-proof. The magnetic property of the material of the spheres involves strong magnetization when it is exposed to an external magnetic field, and little remanence when the external magnetic field is removed. The manufacturing process of the column matrix of magnetic retention material involves sphere packing the column matrix using a vibrator, applying lacquer to the column matrix, gravity draining the lacquer, centrifugation to get rid of any remaining lacquer, air blowing, and re-centrifugation. The steps of air blowing and centrifugation may be repeated several times until all residual lacquer is removed. The column matrix is then placed inside an oven at 100 degrees Celsius for three days. After the column matrix is completely cured, the column matrix held together by the applied lacquer. The magnetizable column matrix, which is packed with spheres, may serve as a magnetic intensifier to intensify the magnetic field gradient as much as 10,000 times. The intensified magnetic field gradient helps attract nano-sized bead-labelled cells to the spheres in the presence of an external magnetic field. The column matrix demagnetizes after the removal of the external magnetic field, which allows the nano-sized bead-labelled cells to be released from the column matrix. The nano-sized bead-labelled cells are then eluted with the flow of rinsing fluid through the column matrix.

Dynabeads are larger superparamagnetic particles made from a synthetic polymer. Since Dynabeads are much larger than Miltenyi nano-sized beads, Dynabeads have a much higher magnetic momentum than Miltenyi nano-sized beads when placed in a magnetic field. Thus, the use of Dynabeads with magnetic cell isolation does not involve a magnetic intensifier, such as a magnetic column matrix. A tube-based system is typically used with Dynabead-labelled cells, where a permanent magnet is placed close to the tube. Target cells labeled with Dynabeads are attracted to the wall of the tube, and the non-labelled cells may then be removed with buffer or media. Other beads of different sizes are also commercially available besides Miltenyi nano-sized microbeads and Dynabeads.

The magnetic isolation device may use a magnetic field generator, e.g., a pair of permanent magnets, along with a magnetic cell isolation holder and accompanying magnetic cell retention materials, flow tubing, collection and preparation vessels, and other components of the disclosed system 100. Further, certain of these components may be provided as single-use components, disposable components, and/or packaged a kit.

In one embodiment, a dedicated kit may be provided to achieve magnetic isolation for a particular particle type. For any specific isolation event, a kit optimized for one or more particles sizes may be provided. The kits may include an appropriate magnetic retention material, which may be preloaded into an appropriately configured magnetic cell isolation holder. In this manner, the user cannot inadvertently load or couple an incorrect magnetic retention material into the passage of magnetic isolation holder. In an embodiment for use with Miltenyi microbeads, a magnetic retention column in a passage of a magnetic isolation holder may be positioned, when loaded, to be in the center of the gap or space between the permanent magnets of a magnetic field generator and associated with a highest or higher magnetic field strengths (i.e., greater than 0.45 T). In another embodiment, magnetic retention tubing for Dynabead) may be positioned in a highest gradient area in between the permanent magnets. The Dynabeads isolation may be performed in conjunction with a magnetic isolation holder with a passage positioned relative to a magnetic field generator to experience both magnetic field strength (i.e., greater than 0.1 T) and magnetic field gradient (i.e., greater than 40 T/m) suitable for retention.

When used in conjunction with the disclosed techniques, the average recovery and average purity of CD3+ using the magnetic isolation device are each approximately greater than 80% for Miltenyi nano-sized beads. For Dynabeads, the average recovery of CD3+ using the magnetic isolation device is approximately 60% and the average purity of CD3+ using the magnetic isolation device is approximately greater than 70%.

Technical effects of the disclosure include providing holders for magnetic isolation of cells for use with a magnetic field generator to enable cell isolation without adjustment of magnetic field parameters between procedures using magnetic particles of different sizes. Additionally, the magnetic isolation device may perform the methods of cell preparation, magnetic cell isolation, and cell elution automatically for each of the different-sized particles to eliminate or reduce user interaction and manipulation of source material.

This written description uses examples, including the best mode, and also to enable any person skilled in the art to practice the invention, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
   a magnetic field generator configured to generate a magnetic field;
   a first holder configured to be removably coupled to the magnetic field generator, the first holder comprising a first passage configured to be positioned within the magnetic field at a first location when the first holder is coupled to the magnetic field generator; and
   a second holder configured to be removably coupled to the magnetic field generator, the second holder comprising a second passage configured to be positioned within the magnetic field at a second location when the second holder is coupled to the magnetic field generator,
   wherein:
   the first passage experiences a first magnetic field strength and a first magnetic field gradient, within the magnetic field at the first location; and
   the second passage experiences a second magnetic field strength and a second magnetic field gradient, within the magnetic at the second location, and wherein the second magnetic field strength is different than the first magnetic field strength or the second magnetic field gradient is different than the first magnetic field gradient, or a combination thereof.

2. The system of claim 1, wherein the magnetic field generator is coupled to a frame, the frame conducting magnetic flux and forming a receiving area configured to receive the first holder or the second holder.

3. The system of claim 2, wherein the receiving area is sized to receive only one of the first holder or the second holder at a given time.

4. The system of claim 2, wherein the receiving area is configured to receive only a portion of the first holder or the second holder.

5. The system of claim 4, wherein the portion comprises the first passage of the first holder or the second passage of the second holder.

6. The system of claim 2, wherein the frame comprises a retractable portion that reduces the magnetic flux generated by the magnetic field generator from going beyond the receiving area while the first holder is uncoupled to the magnetic field generator.

7. The system of claim 6, wherein the retractable portion comprises a spring that compresses to allow the first holder to enter the receiving area of the frame.

8. The system of claim 1, wherein, when the first holder is not coupled to the magnetic field generator, the first passage does not experience the first magnetic field strength.

9. The system of claim 2, wherein the first holder comprises a first end surface configured to abut a stopping portion of the frame when the first holder is coupled to the magnetic field generator.

10. The system of claim 9, wherein the second holder comprises a second end surface configured to abut the stopping portion of the frame when the second holder is coupled to the magnetic field generator, and wherein a first distance between the first end surface and the first passage is different than a second distance between the second end surface and the second passage.

11. The system of claim 1, wherein a first passage and the second passage are different sizes.

12. The system of claim 1, wherein the first holder is configured to be fluidically coupled to a first source of a first size bead, and wherein the second holder is configured to be fluidically coupled to a second source of a second size bead.

13. The system of claim 12, wherein a diameter of the first size bead is less than 1 μm and a diameter of the second size bead greater than 2 μm.

14. The system of claim 12, wherein the first size bead is bound to a target cell within a first cell mixture and the second size bead is bound to a target cell within a second cell mixture.

15. The system of claim 1, wherein the first passage or the second passage comprises a magnetic intensifier.

16. A system, comprising:
a first kit comprising:
a plurality of first size beads; and
a first holder comprising a first passage configured to receive the plurality of first size beads, the first passage positioned within the first holder such that, when the first holder is removably coupled to a magnetic field generator generating a magnetic field, the first holder is positioned within the magnetic field at a first location; and
a second kit comprising:
a plurality of second size beads; and
a second holder comprising a second passage configured to receive the plurality of second size beads, the second passage positioned within the second holder such that, when the second holder is removably coupled to the magnetic field generator generating the magnetic field, the second holder is positioned within the magnetic field at a second location different than the first location;
wherein:
the first passage experiences a first magnetic field strength and a first magnetic field gradient within the magnetic field at the first location; and
the second passage experiences a second magnetic field strength and a second magnetic field gradient within the magnetic field at the second location, and wherein the second magnetic field strength is different than the first magnetic field strength or the second magnetic field gradient is different than the first magnetic field gradient, or a combination thereof.

17. A method for isolating target cells, comprising:
positioning a first holder having a first passage within a receiving area of a frame coupled to a magnetic field generator;
generating a first magnetic field in the receiving area by the magnetic field generator when the first holder is coupled to the magnetic field generator to cause the first passage to experience a first magnetic field strength, a first magnetic field gradient, or both;
positioning a second holder having a second passage within the receiving area, wherein the first passage and the second passage are positioned at different locations within the receiving area; and
generating a second magnetic field in the receiving area by the magnetic field generator when the second holder is coupled to the magnetic field generator to cause the second passage to experience a second magnetic field strength, a second magnetic field gradient, or both.

18. The method of claim 17, wherein the first magnetic field and the second magnetic field are generated from the magnetic field generated by the magnetic field generator.

19. The method of claim 17, wherein, when the first holder is positioned within the receiving area of the frame, the second holder is not positioned within the receiving area of the frame, and when the second holder is positioned within the receiving area of the frame, the first holder is not positioned within the receiving area of the frame.

20. The method of claim 17, further comprising:
incubating a first cell mixture with a first size bead and a second cell mixture with a second size bead such that a target cell in the first cell mixture is labelled with the first size bead and a target cell in the second cell mixture is labelled with the second size bead; and
passing the first cell mixture through the first passage and the second cell mixture through the second passage.

\* \* \* \* \*